United States Patent
Choi et al.

(10) Patent No.: US 11,266,834 B2
(45) Date of Patent: Mar. 8, 2022

(54) ELECTRO-ACUPUNCTURE (EA) SYSTEM HAVING A WEARABLE ELECTRO-ACUPUNCTURE NEUROSTIMULATOR FOR ENHANCED CLINICAL AND SCIENTIFIC OUTCOMES, AND A METHOD

(71) Applicant: BOARD OF SUPERVISORS OF LOUISIANA STATE UNIVERSITY AND AGRICULTURAL AND MECHANICAL COLLEGE, Baton Rouge, LA (US)

(72) Inventors: Jin-Woo Choi, Baton Rouge, LA (US); Jose Aquiles Parodi Amaya, Winter Springs, FL (US); Ronald Koh, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 93 days.

(21) Appl. No.: 16/586,070

(22) Filed: Sep. 27, 2019

(65) Prior Publication Data
US 2020/0101287 A1 Apr. 2, 2020

Related U.S. Application Data

(60) Provisional application No. 62/738,740, filed on Sep. 28, 2018.

(51) Int. Cl.
*A61N 1/36* (2006.01)
*A61N 1/375* (2006.01)

(52) U.S. Cl.
CPC ....... *A61N 1/36017* (2013.01); *A61N 1/3603* (2017.08); *A61N 1/36196* (2013.01); *A61N 1/36007* (2013.01); *A61N 1/3752* (2013.01)

(58) Field of Classification Search
CPC .......................... A61N 1/0502; A61N 1/36017
See application file for complete search history.

(56) References Cited

U.S. PATENT DOCUMENTS 10,154,922 B1 * 12/2018 Perez ................. A61N 1/36017
10,668,286 B2 6/2020 Amaya
(Continued)

*Primary Examiner* — George R Evanisko
(74) *Attorney, Agent, or Firm* — Thomas | Horstemeyer, LLP

(57) ABSTRACT

An electro-acupuncture (EA) system and method for performing EA on a patient are provided. The EA system comprises a wearable neurostimulator device, at least a first pair of electrically-conductive acupuncture needles and a system controller. The wearable neurostimulator device comprises a casing, an EA circuit mechanically coupled to the casing, and an attachment device mechanically coupled to the casing and adapted to removably secure the wearable neurostimulator device to the patient. The first pair of electrically-conductive acupuncture needles is mechanically coupled to the casing and electrically coupled to the EA circuit. The system controller is in communication with the EA circuit of the wearable neurostimulator device via a communication link and controls the EA circuit to cause the EA circuit to output an output voltage selected by the system controller at a frequency selected by the system controller.

20 Claims, 11 Drawing Sheets

(56) References Cited

U.S. PATENT DOCUMENTS

| | | | | |
|---|---|---|---|---|
| 2006/0079946 A1* | 4/2006 | Gavronsky | ........ | A61N 1/36021 607/46 |
| 2008/0091248 A1* | 4/2008 | Libbus | .................. | A61N 1/365 607/60 |
| 2014/0236258 A1* | 8/2014 | Carroll | ................. | A61N 1/0476 607/46 |
| 2017/0216576 A1* | 8/2017 | Gregson | .............. | A61N 1/0524 |
| 2018/0055410 A1* | 3/2018 | Ding | ................... | A61H 39/002 |

* cited by examiner

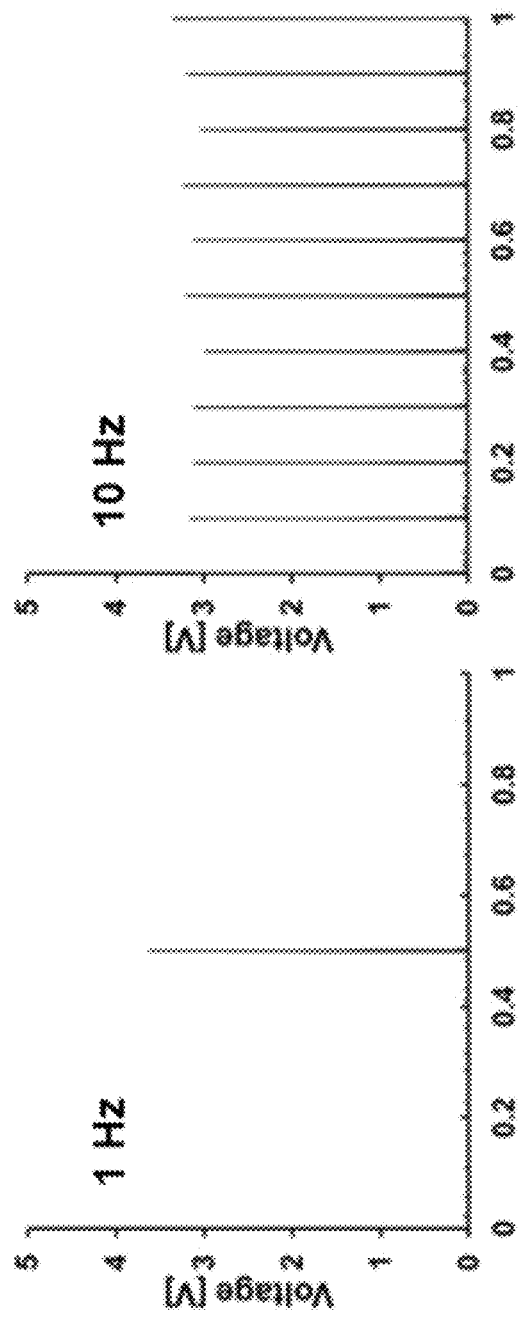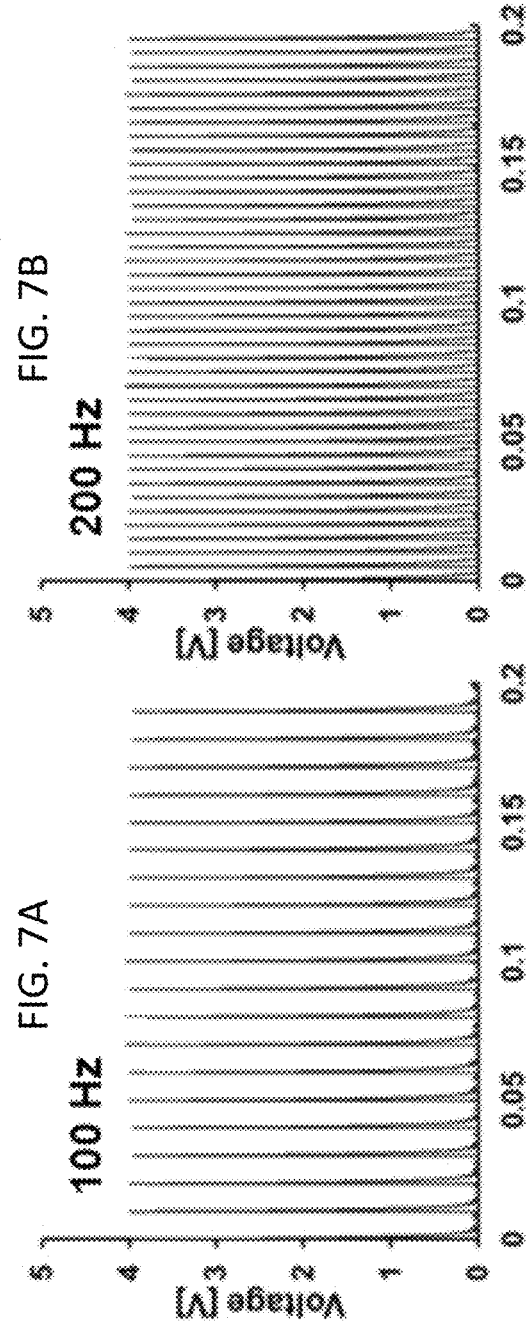
FIG. 7A  FIG. 7B  FIG. 7C  FIG. 7D
ELECTRO-ACUPUNCTURE (EA) SYSTEM HAVING A WEARABLE ELECTRO-ACUPUNCTURE NEUROSTIMULATOR FOR ENHANCED CLINICAL AND SCIENTIFIC OUTCOMES, AND A METHOD

CROSS-REFERENCE TO RELATED APPLICATIONS

The present application is a nonprovisional application that claims priority to, and the benefit of the filing date or, U.S. provisional application having Ser. No. 62/738,740, filed on Sep. 28, 2018, entitled "An Electro-Acupuncture (EA) System Having A Wearable Electro-Acupuncture Neurostimulator For Enhanced Clinical And Scientific Outcomes, And A Method," which is hereby incorporated by reference herein in its entirety.

TECHNICAL FIELD

The present disclosure relates to electro-acupuncture (EA), and more particularly, to an EA system having a wearable EA neurostimulator device.

BACKGROUND

Acupuncture is a method for treating conditions through stimulation of specific points in the body that lie on nerve pathways or motor control areas. Stimulation can be performed through various methodologies, and electro-acupuncture (EA) has increased in interest due to the ease of use of electrical stimulation machines. EA is a growing field with diverse medical applications. Medical conditions treated include pain management, cancer symptoms, musculoskeletal, neurological, obstetric, gastrointestinal, cardiovascular, and surgical anesthesia. While many studies have been conducted, significant challenges remain in the scientific study of medical applications of EA.

One of the problems with scientific studies of EA is that acupuncture techniques and stimulation parameters can differ depending on clinician experience, personal preference, and individual pain tolerance. Additionally, known EA stimulation machines are large and heavy, which requires the patient—human or animal—to remain relatively motionless during treatment. This can cause undesired stress responses in animals, or require sedation of the animal. Both of these options fundamentally change the physiological condition of the patient and can affect the outcome of the experimental procedure.

SUMMARY

Representative embodiments are directed to an EA system and method for performing EA on a patient. The EA system comprises a wearable neurostimulator device, at least a first pair of electrically-conductive acupuncture needles and a system controller. The wearable neurostimulator device comprises a casing, an EA circuit mechanically coupled to the casing, and an attachment device mechanically coupled to the casing and adapted to removably secure the wearable neurostimulator device to the patient. The first pair of electrically-conductive acupuncture needles is electrically coupled to a first pair of output terminals of the EA circuit. The system controller is in communication with the EA circuit of the wearable neurostimulator device via a communication link and controls the EA circuit by sending at least a first set of setting information to the EA circuit over the communication link to cause the EA circuit to output at least a first output voltage at a first frequency from the first pair of output terminals in accordance with the first set of setting information selected by the system controller.

In accordance with an embodiment, the system controller comprises a smartphone and the communication link is a wireless communication link, such as a Bluetooth Low Energy (BLE) communication link. The smartphone comprises at least a first processor and a memory device. The first processor is configured to perform an EA application program that processes information input to the smartphone by a user and sends communications to the wearable neurostimulator device of the EA system to control settings of an EA circuit of the wearable neurostimulator device in accordance with the information input to the smartphone by the user. The settings include at least an output voltage of the EA circuit that is output from the wearable neurostimulator device at one or more output terminals of the wearable neurostimulator device and a frequency of the output voltage.

In accordance with an embodiment, the memory device stores home-use setting information input to the smartphone by the user. The home-use setting information is associated with use of the EA system at a location that is remote to the user who configured the smartphone. When the smartphone is powered on at the remote location, the home-use setting information is retrieved from the memory device and sent by the smartphone to the wearable neurostimulator device to cause the output voltage of the EA circuit and the frequency of the output voltage to be set according to the home-use setting information.

The method, in accordance with an embodiment, for performing EA on a patient with an EA system comprises:
  with a system controller of the EA system, sending at least a first set of setting information over a communication link;
  in an EA circuit of a wearable neurostimulator device of the EA system worn by a patient, receiving the first set of setting information sent over the communication link by the system controller; and
  in the EA circuit of the wearable neurostimulator device, setting at least a first output voltage of the EA circuit and a first frequency of the first output voltage according to the received first set of setting information.

These and other features and advantages will become apparent from the following description, drawings and claims.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

FIGS. 7A-7D are time vs. output voltage plots of the output voltage of the circuit shown in FIG. 3 for stimulation frequencies of 1 Hertz (Hz), 10 Hz, 100 Hz and 200 Hz, respectively.

DETAILED DESCRIPTION

Figure 1:
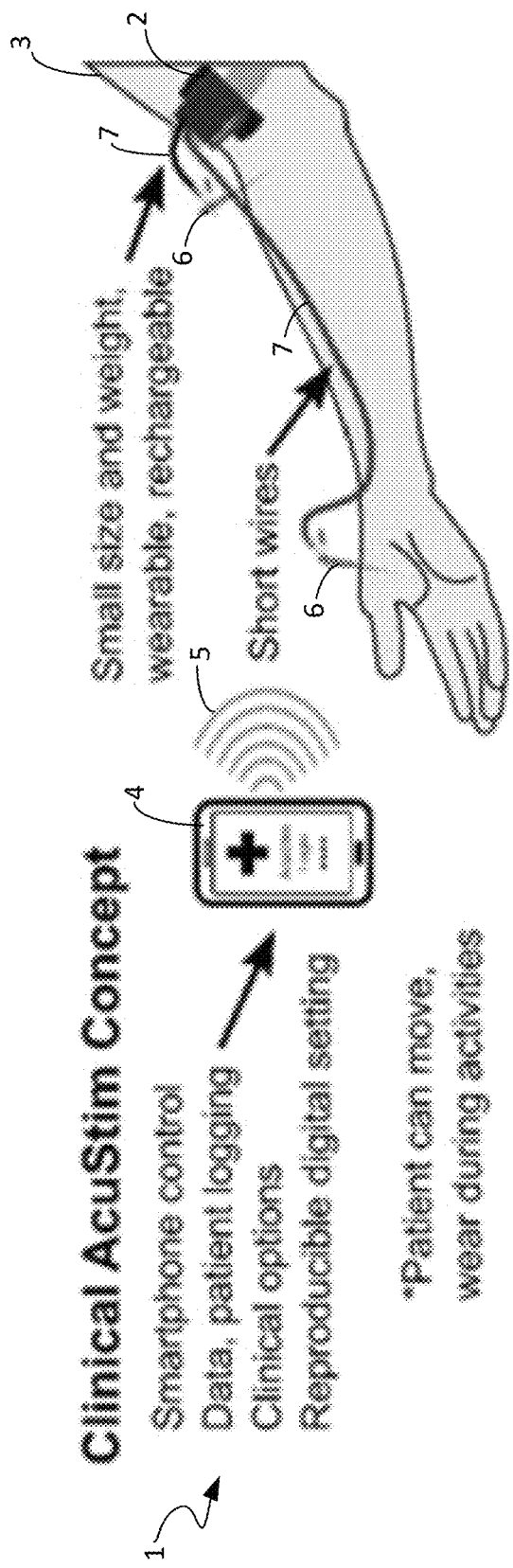
FIG. 1 is a pictorial diagram of the EA system in accordance with a representative embodiment.

The present disclosure discloses an EA system and method for performing EA on a patient. The EA system comprises a wearable neurostimulator device, at least a first pair of electrically conductive acupuncture needles and a system controller. The wearable neurostimulator device comprises a casing, an EA circuit mechanically coupled to the casing, and an attachment device mechanically coupled to the casing and adapted to removably secure the wearable neurostimulator device to the patient. The first pair of electrically-conductive acupuncture needles is mechanically coupled to the wearable neurostimulator device and is electrically coupled to the EA circuit of the wearable neurostimulator device. The system controller is in communication with the EA circuit of the wearable neurostimulator device via a communication link and controls the EA circuit to cause the EA circuit to output at least a first output voltage selected by the system controller at a first frequency selected by the system controller to the first pair of electrically-conductive acupuncture needles in accordance with the setting information.

In accordance with a preferred embodiment, the communication link is a wireless communication link, such as a Bluetooth wireless communication link, for example, and the system controller comprises a smartphone that executes an EA application program to control the EA circuit.

From the points of view of the clinician and scientist, known EA machines are not designed for modern experimental conditions that take advantage of computational power of smartphones or computers. A solution is desired that tackles these problems, and provides a better approach for clinicians and scientists alike. A few representative embodiments of the system and method that provide such an EA solution will now be described with reference to FIGS. 1-11, in which like reference numerals represent like components, elements or features. It should be noted that features, elements or components in the figures are not intended to be drawn to scale, emphasis being placed instead on demonstrating inventive principles and concepts. It should be noted that the inventive principles and concepts are not limited to the representative embodiments described herein, as will be understood by those of skill in the art in view of the description provided herein.

In the following detailed description, for purposes of explanation and not limitation, exemplary, or representative, embodiments disclosing specific details are set forth in order to provide a thorough understanding of inventive principles and concepts. However, it will be apparent to one of ordinary skill in the art having the benefit of the present disclosure that other embodiments according to the present teachings that are not explicitly described or shown herein are within the scope of the appended claims. Moreover, descriptions of well-known apparatuses and methods may be omitted so as not to obscure the description of the exemplary embodiments. Such methods and apparatuses are clearly within the scope of the present teachings, as will be understood by those of skill in the art. It should also be understood that the word "example," as used herein, is intended to be non-exclusionary and non-limiting in nature.

The terminology used herein is for purposes of describing particular embodiments only, and is not intended to be limiting. The defined terms are in addition to the technical, scientific, or ordinary meanings of the defined terms as commonly understood and accepted in the relevant context.

The terms "a," "an" and "the" include both singular and plural referents, unless the context clearly dictates otherwise. Thus, for example, "a device" includes one device and plural devices. The terms "substantial" or "substantially" mean to within acceptable limits or degrees acceptable to those of skill in the art. For example, the term "substantially parallel to" means that a structure or device may not be made perfectly parallel to some other structure or device due to tolerances or imperfections in the process by which the structures or devices are made. The term "approximately" means to within an acceptable limit or amount to one of ordinary skill in the art. Relative terms, such as "over," "above," "below," "top," "bottom," "upper" and "lower" may be used to describe the various elements' relationships to one another, as illustrated in the accompanying drawings. These relative terms are intended to encompass different orientations of the device and/or elements in addition to the orientation depicted in the drawings. For example, if the device were inverted with respect to the view in the drawings, an element described as "above" another element, for example, would now be below that element.

Relative terms may be used to describe the various elements' relationships to one another, as illustrated in the accompanying drawings. These relative terms are intended to encompass different orientations of the device and/or elements in addition to the orientation depicted in the drawings.

The term "memory" or "memory device", as those terms are used herein, are intended to denote a non-transitory computer-readable storage medium that is capable of storing computer instructions, or computer code, for execution by one or more processors. References herein to "memory" or "memory device" should be interpreted as one or more memories or memory devices. The memory may, for example, be multiple memories within the same computer system. The memory may also be multiple memories distributed amongst multiple computer systems or computing devices.

A "processor" or "processing device," as those terms are used herein encompass an electronic component that is able to execute a computer program or executable computer instructions. References herein to a system comprising "a processor" or "a processing device" should be interpreted as a system having one or more processors or processing cores. The processor may for instance be a multi-core processor. A processor may also refer to a collection of processors within a single computer system or distributed amongst multiple computer systems. The term "computer," as that term is used herein, should be interpreted as possibly referring to a single computer or computing device or to a collection or network of computers or computing devices, each comprising a processor or processors. Instructions of a computer program can be performed by a single computer or processor or by multiple processors that may be within the same computer or that may be distributed across multiple computers.

FIG. 1 is a pictorial diagram illustrating some of the features of the EA system 1 in accordance with a representative embodiment. In accordance with this representative embodiment, the EA system 1 comprises a wearable neurostimulator device 2 designed to be worn by the patient 3 during treatment, a system controller 4 that controls the wearable neurostimulator device 2 and communicates with the wearable neurostimulator device 2 via a wireless communication link 5 and one or more electrically conductive acupuncture needles 6 that are mechanically coupled via one or more lead wires 7 to the wearable neurostimulator device 2 and electrically coupled via the lead wires 7 to an EA circuit (FIG. 2) of the wearable neurostimulator device 2. In accordance with this representative embodiment, the system controller 4 is a smartphone and the wireless communication link 5 is Bluetooth link. The system controller 4 and the wireless communication link 5 will be referred to hereinafter as the smartphone 4 and the Bluetooth link 5, respectively. Persons of skill in the art will understand, in view of the description provided herein, that the wireless communication link 5 may any suitable wireless communication link and that the system controller 4 may be any suitable system controller. Thus, the inventive principles and concepts are not limited to using a smartphone and a Bluetooth link as the system controller 4 and the wireless communication link 5, respectively, as will be understood by those of skill in the art in view of the description provided herein.

The small, light-weight size and wearable nature of the wearable neurostimulator device 2 allow the patient 3 to move around and resume normal activities during treatment. This feature is especially important in veterinary applications to reduce stress on the animal. The control of the wearable neurostimulator device 2 via the smartphone 4 allows for precise adjustment of stimulation pulse voltage and frequency. This feature combined with the data processing capabilities of the smartphone 4 allows easy logging of patient and treatment data.

In the following discussion, a representative embodiment of the circuit and smartphone application program (app) design of the EA system 1 is provided. The discussion includes a discussion of the use the EA system 1 in an EA animal study to verify the correct operation of the EA system 1 as an EA stimulation machine.

Design of EA Circuit

Overview of Circuit Design for Single-Channel Configuration

Figure 2:
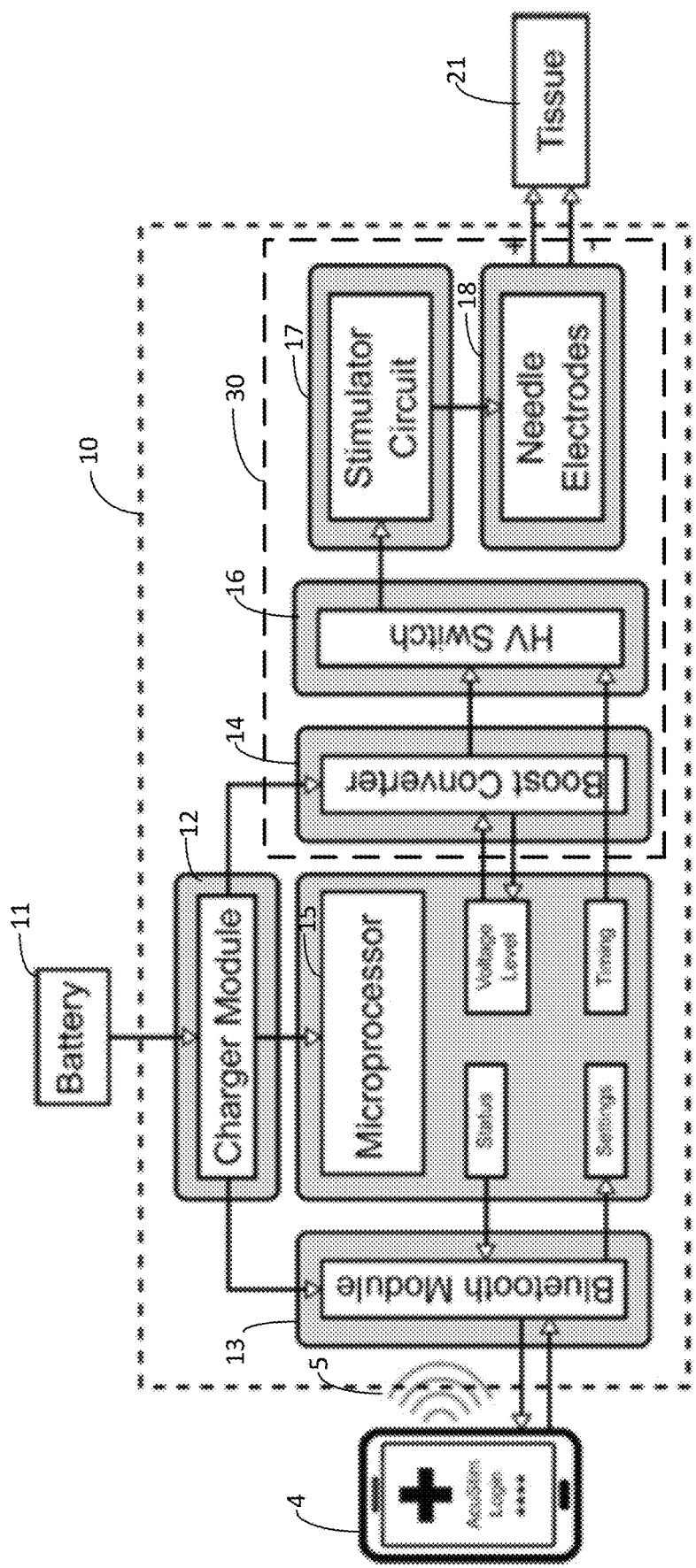
FIG. 2 is a block diagram of the EA circuit of a wearable neurostimulator device of the EA system shown in FIG. 1 in accordance with a representative embodiment.

FIG. 2 is a block diagram of the EA circuit 10 of the wearable neurostimulator device 2 of the EA system 1 shown in FIG. 1 in accordance with a representative embodiment. Power input is a battery 11 (e.g., a 3.7V lithium polymer battery) delivered to a battery charger module 12. Power is then delivered by the battery charger module 12 to a Bluetooth module 13, a boost converter circuit 14, and a processor 15, which may be a microprocessor, a microcontroller, or a state machine, for example. The processor 15 relays device information to the user smartphone 4 over the Bluetooth link 5 via the Bluetooth module 13, which is used for bidirectional communication. The processor 15 then controls the output voltage level of the wearable neurostimulator device 2 via the boost converter 14, and sets the frequency of stimulation generated by a stimulator circuit 17 with a high-voltage (HV) switch 16. The stimulator circuit 17 is a pulse generator circuit that powered by the boost converter 14, and timed by the HV switch 16. A bipolar wire clip (not shown) connects the output of the stimulator circuit 17 to acupuncture needle electrodes 18, the tips of which are inserted in acupoints in tissue 21 of the patient for treatment. Stimulation output design was performed with consultation with a veterinary acupuncturist.

Output Pulse Generator Circuit

A known commercial electro-acupuncture device output was analyzed and the maximum power level output used by the acupuncturist was found to be 3 V across a 1 kΩ load with an approximate duration of 400 µs. For the representative embodiment shown in FIG. 2, the EA circuit 10 was designed to have a maximum output voltage of at least 4 V and a duration of at least 500 µs. It should be noted, however, that the inventive principles and concepts are not limited to the EA system 1 having any particular output power level or duration.

Figure 3:
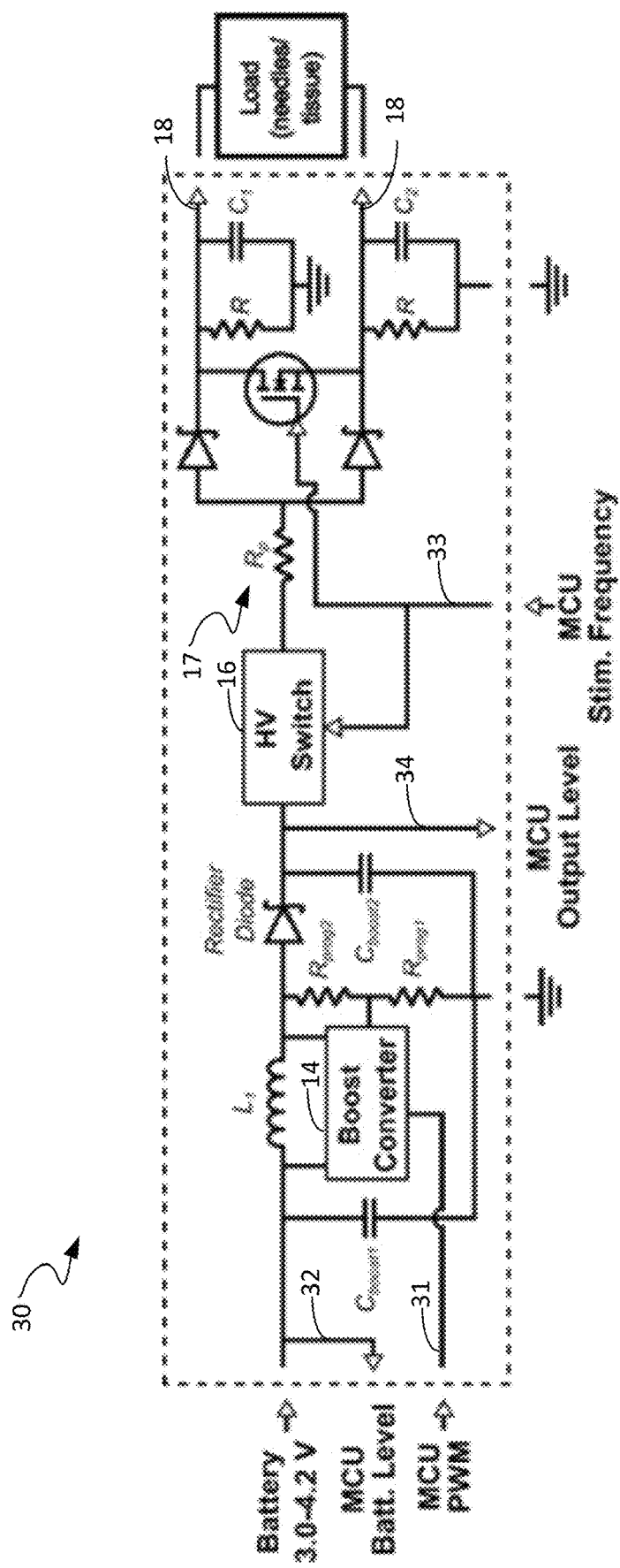
FIG. 3 is a schematic diagram of a portion of the circuit of the wearable neurostimulator device shown in the dashed box labeled with reference numeral 30 in FIG. 2 in accordance with a representative embodiment.

FIG. 3 is a block diagram of the portion of the EA circuit 10 shown in FIG. 2 within dashed box 30, which includes the boost converter 14, the HV switch 16, the stimulator circuit 17, and the needle electrodes 18. In accordance with this embodiment, the boost converter 14 is designed to supply up to 18 V to the HV switch 16. The output level of the boost converter 14 is controlled via a pulse-width modulation (PWM) signal 31 from the processor 15 (FIG. 2). The HV switch 16 is timed with a timing signal 33 from the processor 15. The processor 15 continuously monitors the battery voltage input 32 and the boost converter output level 34, to relay that information to the smartphone 4. In accordance with a representative embodiment, these voltage levels are also used to control light emitting diodes (LEDs) (not shown) for visual indication to the user.

PCB and Case

Figure 4A:
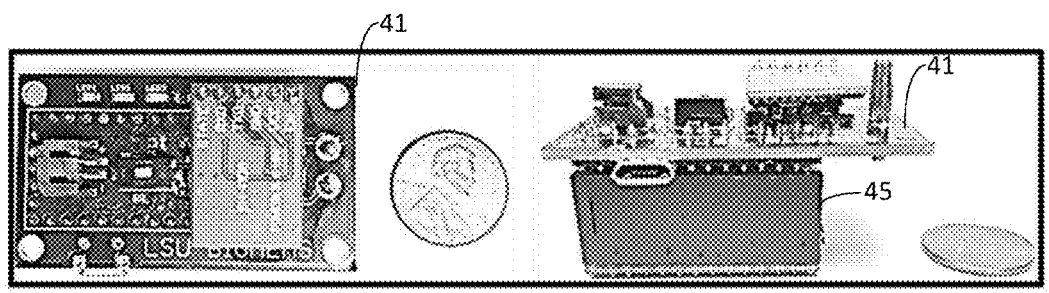
FIG. 4A shows top and side view photographs of a printed circuit board (PCB) of a prototype of the wearable neurostimulator device shown in FIG. 1 in accordance with a representative embodiment.
Figure 4B:
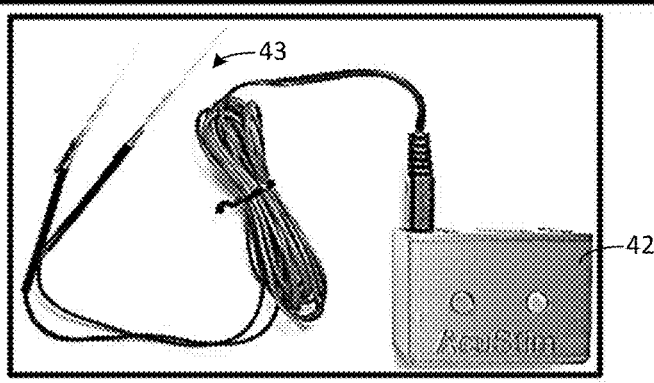
FIG. 4B is a top view photograph of a case or housing of the wearable neurostimulator device shown in FIG. 1 for housing components of the EA system shown in FIG. 2.
Figure 4C:
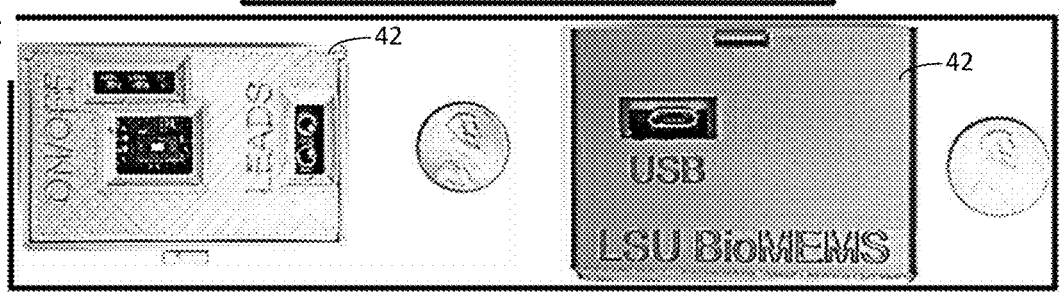
FIG. 4C shows front and back view photographs of the case shown in FIG. 5B.
Figure 4D:
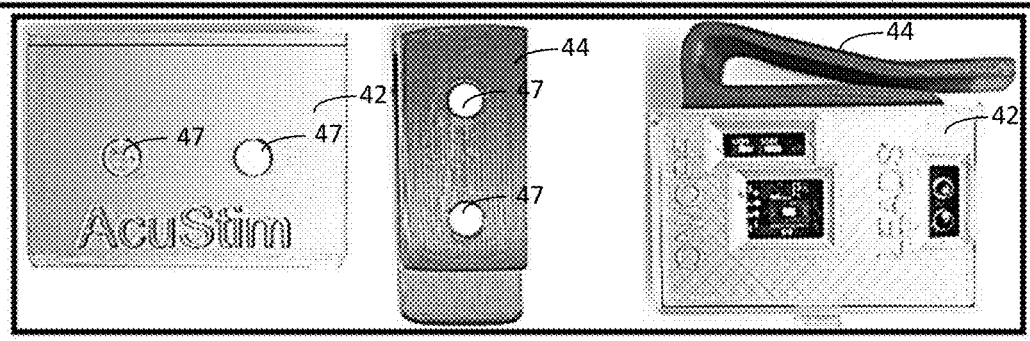
FIG. 4D shows front and back view photographs of the case shown in FIG. 5C along with an attachment device that can be used to secure the wearable neurostimulator device to a patient.

FIGS. 4A-4D are photographs of a first prototype of the wearable neurostimulator device 2 from different view angles. FIG. 4A shows top and side view photographs of a printed circuit board (PCB) of the prototype of the wearable neurostimulator device 2 shown in FIG. 1 in accordance with a representative embodiment. FIG. 4B is a top view photograph of a case or housing 42 of the wearable neurostimulator device 2 shown in FIG. 1 for housing components of the EA system 1 shown in FIG. 2. In FIG. 4B, the case 42 is shown mechanically coupled via a plug jack to a pair of acupuncture needles 43. FIG. 4C shows front and back view photographs of the case 42 shown in FIG. 4B. FIG. 4D shows front and back view photographs of the case 42 shown in FIG. 4C along with an attachment device 44 that can be used to secure the wearable neurostimulator device 2 to a patient.

The case 42 has a shape, size and weight selected to allow the wearable neurostimulator device 2 to be easily and comfortably worn on the patient's body. For example, the case 42 may be attached by the attachment device 44 or by any suitable attachment device to the patient's belt in the case where the patient is a human being, or to a collar in the case where the patient is an animal. In accordance with this representative embodiment, the EA circuit 10 shown in FIG. 2 is implemented in the PCB 41, which is attached vertically to a pin-out board 45 on which the processor 15 (FIG. 2) and Bluetooth module 13 (FIG. 2) are mounted. In accordance with this representative embodiment, the dimensions of the case 42 are 56 mm×35 mm×41 mm and the weight of the wearable neurostimulator device 2, including the case 42 with the PCB 41, the pin-out board 45 housed therein, the attachment device 44 secured thereto, the battery 11 (FIG. 3) and a set of electrical leads, is 75 grams. A 500 mA, 3.7 V lithium polymer battery was used for this embodiment of the EA system 1.

The inventors also investigated the clinical setting and discussed with clinicians usage of the wearable neurostimulator device 2 in order to determine typical requirements for battery life, pulse characteristics, interface type, and case design. Although minimum battery life is thirty minutes for a typical EA treatment session, the inventors decided that a charge should last for at least one day of treatment sessions. The wearable neurostimulator device 2 is not limited with respect to the battery that is used to power the device or with respect to battery life. For example, each wearable neurostimulator device 2 may be used for approximately one thirty-minute treatment session per hour, which results in 4.5 hours of usage for a typical nine hour work day. Stimulation frequency should be variable, and the most commonly used frequencies lie between 2 Hz and 100 Hz. For the first prototype shown in FIGS. 4A-4D, the interface was designed to be of the type preferred by clinicians, which is 2 mm banana plug jack bipolar alligator clips that clamp onto the acupuncture needles 43 (FIG. 4B).

Because the case 42 is designed to be worn by the patient, the wearable neurostimulator device 2 was designed so that the settings would not accidentally be altered during treatment. The case 42 was also designed so that the wearable neurostimulator device 2 would not tangle and break the electrodes 43 or the wearable neurostimulator device 2 and so that it could not harm the patient. In accordance with this representative embodiment, the case 42 has three LEDs for visual status indication to the user (e.g., charging, finished charging, and device status), and one recessed main power switch with a charging port on the side (FIG. 4C). In accordance with a representative embodiment, the settings can only be changed in the app executed by the smartphone 4 used by the clinician. In the prototype shown in FIGS. 4A-4D, the case 42 attaches to a belt clip of the patient or via neodymium magnets 47 such that if tangling of the wires 43 or impact to the case 42 occurs, the case 42 can be safely and easily detached.

Smartphone App Design

Figure 5B:
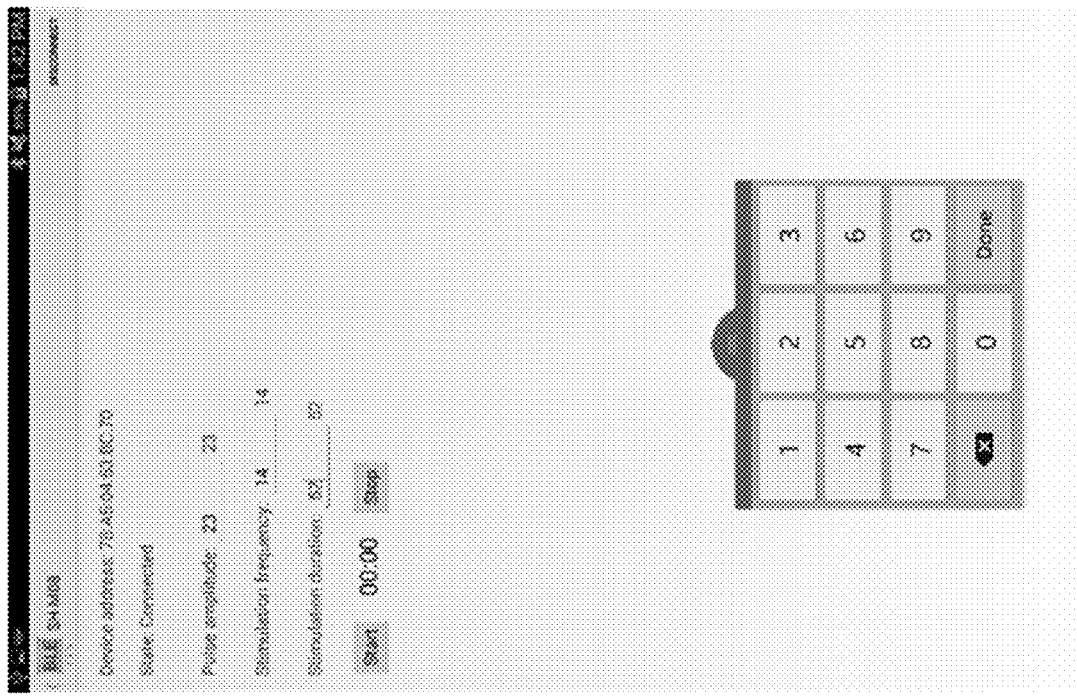
FIGS. 5A and 5B show the initial settings displayed and the settings displayed during a treatment session, respectively, on the display of the smartphone shown in FIG. 1 in accordance with a representative embodiment.
Figure 5A:
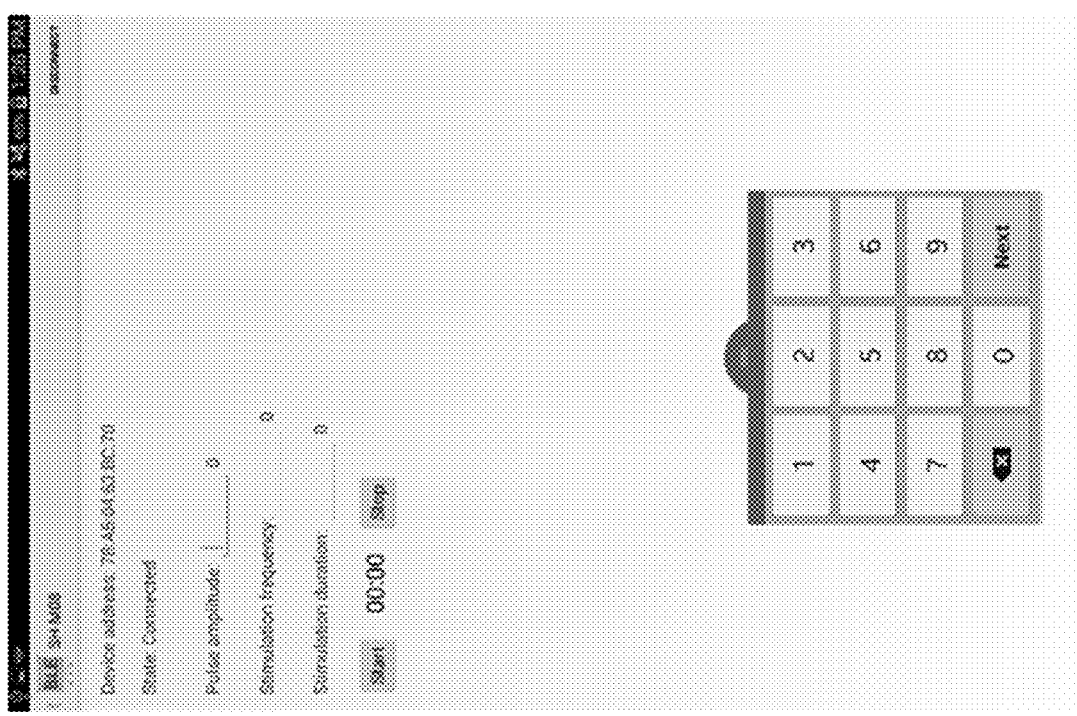

As indicated above, a smartphone app was developed to control the EA system 1. For communication between the smartphone 4 and the wearable neurostimulator device 2, the inventors used a Bluetooth Low Energy (BLE) protocol because of its reduced energy consumption, but other types of wireless protocols may be used. Under control of this app, the main screen of the smartphone 4 displays all the control buttons and the current values of the voltage output, stimulation frequency and duration of stimulation. FIGS. 5A and 5B show the initial settings displayed and the settings displayed during a treatment session, respectively, on the display of the smartphone 4 in accordance with a representative embodiment. In accordance with this embodiment, the user simply changes the values of the parameters and presses the "Start" button to commence stimulation. With the BLE protocol, the wearable neurostimulator device 2 was configured as the server so that the smartphone 4 makes requests to the wearable neurostimulator device 2 for updating the stimulation parameters. In accordance with this representative embodiment, once treatment is started, the wearable neurostimulator device 2 operates independently of the smartphone 4 in case the Bluetooth connection is lost, and will carry out stimulation for the duration set during the programming. It should be noted, however, that the inventive principles and concepts are not limited with respect to the type or amount of information that is displayed on the display of the smartphone 4, as will be understood by those of skill in the art in view of the description provided herein. The display of the smartphone 4 provides an interface between the EA system 1 and the user that can provide any desired information to the user to assist the user in using and/or configuring the EA system 1.

Measurement Results and Discussion

Smartphone Control of Output Voltage

Figure 6B:
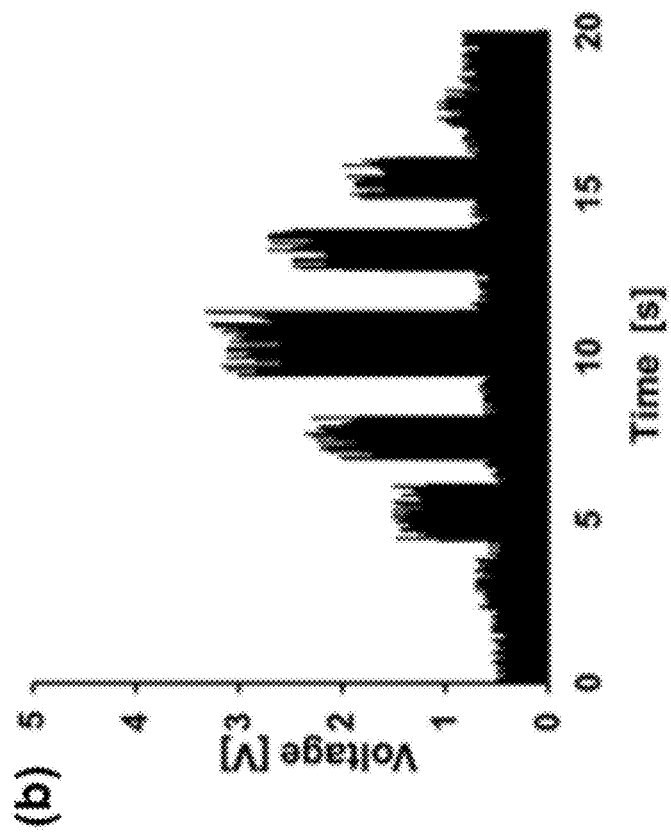
FIGS. 6A and 6B are time vs. output voltage plots corresponding to measurements made of the output voltage of the circuit shown in FIG. 3 during experimentation for time in milliseconds (ms) and seconds (s), respectively.
Figure 6A:
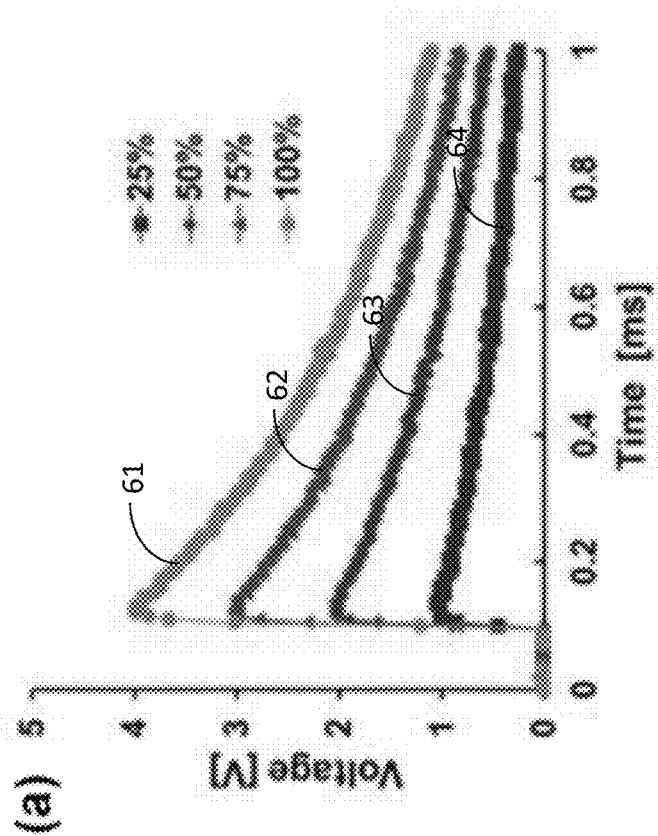

FIGS. 6A and 6B are time vs. output voltage plots corresponding to measurements made of the output voltage of the circuit 10 shown in FIG. 2 during experimentation for time in milliseconds (ms) and seconds (s), respectively. The wearable neurostimulator device 2 was connected to acupuncture needle clips, and voltage was measured across a 1 kΩ load (FIG. 6A). The output voltage was controlled via the smartphone 4, and was continuously measured to verify operation of the voltage control (FIG. 6B). The curves 61-64 shown in FIG. 6A represent the output voltage selected by the user of 25%, 50%, 75% and 100%, respectively. The present output level of the EA system 1 is also shown by the app on the display of the smartphone 4 to allow for repeatability and consistency across patients and/or treatments. Precise controllability of output levels allows for repeatable experimental procedures, and for repeatable and reliable treatment conditions. This type of recording and repeatability, in addition to the stimulation pulse characteristics developed previously by the inventors, are desired for proper reporting of electro-acupuncture results.

Smartphone Control of Stimulation Frequency

Stimulation frequency was also measured with outputs across a 1 kΩ load. FIGS. 7A-7D are plots of output voltage of the EA circuit 10 shown in FIG. 2 as a function of time for stimulation frequencies of 1 Hertz (Hz), 10 Hz, 100 Hz and 200 Hz, respectively. The stimulation frequency was controlled via the smartphone 4, and the current settings preferably are displayed by the app on the display of the smartphone 4. Controllability of stimulation frequency is integral for research and clinical applications of EA devices. The EA system 1 provides for this selectability of the stimulation frequency by the user.

In the veterinary setting, animals typically must be physically restrained or sedated to allow for EA treatment, the placement of needles, and to maintain proximity to benchtop devices. The wearable neurostimulator device 2 of the EA system 1 provides a solution for these issues. Veterinary patients have the additional problem that sedation and holding by a machine or treatment specialist may cause unwanted hormone release, and this may affect the outcome of treatment. Wearable operation solves these issues by allowing patients to move freely while receiving treatment, and also to move to a different location during treatment. With traditional EA systems, movement of the patient will create tension on the cables due to the fact that the EA device is bulky, typically sits at a particular location and does not move as the patient moves, which can cause the needles to be pulled out of the patient. With the wearable neurostimulator device 2, the risk of this happening is eliminated or at least greatly reduced because movement of the patient will not place additional tension on the cables due to the fact that the wearable neurostimulator device 2 moves with the patient. Additionally, the wearable neurostimulator device 2 allows for new treatment methodologies such as take-home EA prescription treatment. In such cases, the wearable neurostimulator device 2 would typically be programmed at the clinic, and then the patient takes it home for treatment over several days. The use of the smartphone 4 also allows for novel features not available in other commercial EA devices such as, for example, secure user login, patient logging, treatment logging, multiple device connectivity, and take-home device programming.

Battery Life

As indicated above, in accordance with an embodiment, the wearable neurostimulator device 2 was powered by a 500 mAh 3.7V lithium polymer battery 11. The EA system 1 was set to output stimulation at maximum output level and 150 Hz stimulation frequency across a 1 k$\Omega$ load with no stop in stimulation. The battery 11 was charged to 4.2 V. The battery voltage was periodically measured, and found to last 300 minutes before it was discharged. This duration is sufficient for the expected use of one day of treatment in a clinical setting (approximately 4.5 hours of stimulation). The battery life can be extended via, for example, microprocessor low-power settings, which were not implemented in this test.

Animal Experiment Validation

Figure 8:
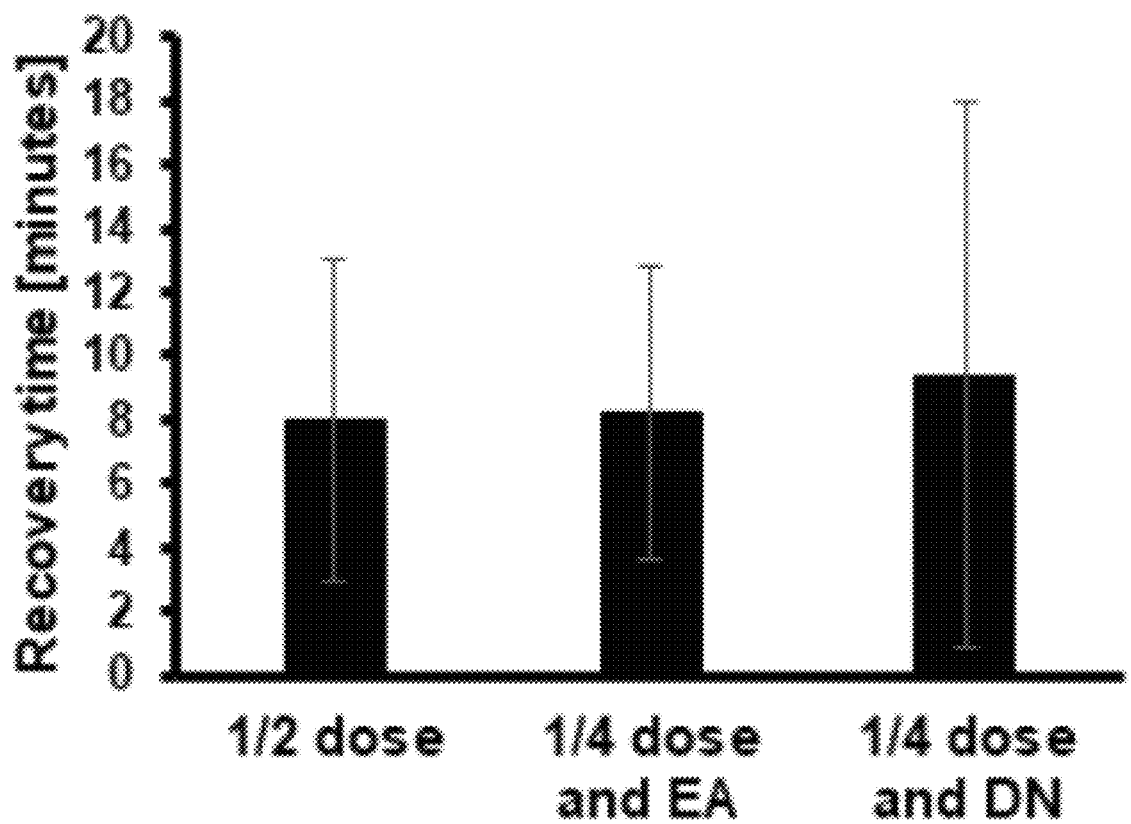
FIG. 8 is a plot of recovery time vs. dosage for the animal experiments that were conducted using the EA system shown in FIG. 1 to verify correct operation of the EA system in EA applications.

FIG. 8 is a plot of dosage vs. recovery time for the animal experiments that were conducted using the EA system 1 shown in FIG. 1 to verify correct operation of the EA system 1 in EA applications. The EA system 1 was utilized in an EA study at the Louisiana State University School of Veterinary Medicine (LSU-SVM). The animal study protocol was approved by the Institutional Animal Care and Use Committee (IACUC) of LSU-SVM. The randomized animal study was performed to determine if EA applied to GV26 and GV1-b (Wei-jian) could be used to lower the dosage amount of atipamezole hydrochloride required for post-surgery anesthesia recovery. In the study, 35 cats were anesthetized using ketamine, dexmedetomidine, and butorphanol tartrate in 1.25:1:1.25 cc ratio mixed with 1.5 cc saline. Dosage of the anesthesia was 20 µg/kg. The manufacturer recommended full dose of atipamezole hydrochloride is equal to the dosage of anesthesia, or 20 µg/kg in the present case. Three groups of cats were treated using one quarter dose atipamezole hydrochloride and EA (12 cats), one quarter dose atipamezole hydrochloride and dry needling (10 cats), or one half dose atipamezole hydrochloride and no acupuncture (13 cats). The time to recover from anesthesia was recorded.

The recovery time for dexmedetomidine reversal with atipamezole hydrochloride in cats has previously been reported by M. Granholm, B. C. McKusick, F. C. Westerholm, and J. C. Aspegrén, "Evaluation of the clinical efficacy and safety of dexmedetomidine or medetomidine in cats and their reversal with atipamezole," Veterinary Anaesthesia and Analgesia, vol. 33, no. 4, pp. 214-223, July 2006. Sedation and analgesic effects were clinically and statistically reduced in 5 minutes, and full recovery was observed at 15 minutes. Dosage in the study was 40 µg/kg dexmedetomidine, and 200 µg/kg atipamezole hydrochloride, or a 5-fold increase in atipamezole hydrochloride compared to the present method.

The animal experiments were used to verify correct operation of the stimulator in EA applications. The ¼ dose atipamezole hydrochloride treatments alone should not be effective in recovering the cats from anesthesia. However, when coupled with dry needling (DN) and EA it can be seen that they have similar effectiveness to using a ½ dose (FIG. 8). These results are comparable with the manufacturer effectiveness results reported in Antisedan(R). Espoo, Finland: Orion Corporation, April 2014. Additionally, these results also support conclusions reported by A. Goe, J. Shmalberg, B. Gatson, P. Bartolini, J. Curtiss, and J. F. X. Wellehan, "EPINEPHRINE OR GV-26 ELECTRICAL STIMULATION REDUCES INHALANT ANESTHESTIC RECOVERY TIME IN COMMON SNAPPING TURTLES (CHELYDRA SERPENTINA)," Journal of Zoo and Wildlife Medicine, vol. 47, no. 2, pp. 501-507, June 2016.

Channel Implementation

Multi-Channel Implementation Requirements

Figure 9:
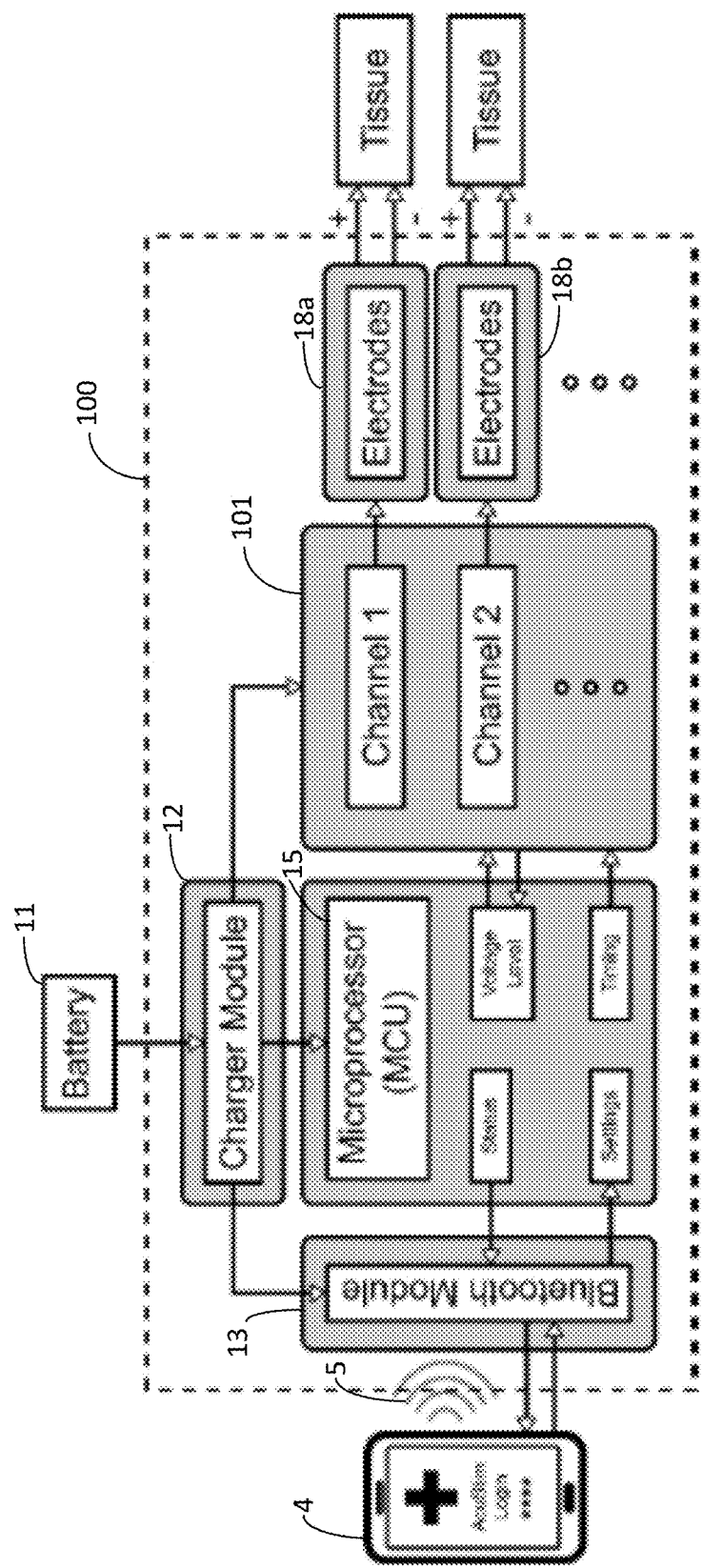
FIG. 9 is a block diagram of the EA circuit of the wearable neurostimulator device of the EA system shown in FIG. 1 in accordance with another representative embodiment in which the EA circuit is configured for multiple-channel (multi-channel) operations.

FIG. 9 is a block diagram of the EA circuit 100 of the wearable neurostimulator device of the EA system 1 shown in FIG. 1 in accordance with another representative embodiment in which the EA circuit 100 is configured for multiple-channel (multi-channel) operations. EA is typically performed on several acupoints simultaneously. Therefore, it is desirable to have a device that outputs independently controlled signals on multiple channels. The block diagram shown in FIG. 9 is a two-channel configuration, but the inventive principles and concepts apply to any N-channel configuration, where N is a positive integer that is greater than one. As will be understood by those of skill in the art in view of the description provided herein, the two-channel configuration can be extended to any N-channel configuration.

In block 101, the Channel 1 and Channel 2 blocks each comprise a boost converter 14, an HV switch 16 and a stimulator circuit 17 as shown in FIGS. 2 and 3. Thus, in accordance with this representative embodiment, each channel has independent voltage amplitude control, frequency output, and stimulation duration. Voltage amplitude is controlled at the boost converter 17 via the duty cycle of one PWM signal (FIG. 3, signal 31) from the processor 15 in the manner described above with reference to FIG. 3. The output frequency is controlled via the frequency of one PWM signal with 50% duty cycle. This frequency is 1-200 Hz for EA applications. Thus, each channel uses two independent PWM signals, one with variable duty cycle, and one with variable frequency. Each channel also includes a pulse generator circuit that determines the output signal waveform. This waveform can be kept the same for each channel, or modified such that different channels have different waveforms.

For the prototype that implements the EA circuit 100, a Teensy 3.2 microprocessor interface board with a MK20DX256VLH7 Cortex M4 processor (Arm, Cambridge, United Kingdom) was used for the processor 15 because of the shield-type interfacing for fast prototype iteration, and because hardware can be programmed in C++ through the Arduino environment. Hardware PWM timers were used to generate the variable frequency PWM signal.

With this board and processor it is possible to implement a design with a maximum of 2 channels using hardware timers alone. The Arduino environment allows for one more channel to be implemented using a software timer that can output a third variable frequency PWM signal. The microprocessor also comes in a model variant with 6 PWM timers, and this device would allow for a 6 channel device to be implemented. In general, the number of channels is limited to the number of hardware timers available, and also limited to the number of pins controlled by these timers. Dedicated PWM drivers can also be used, such as the PIC12F1571 (Microchip, Chandler, Ariz.), which would provide 3 more timers per chip.

PCB and Case for Two-Channel Configuration

Figure 10:
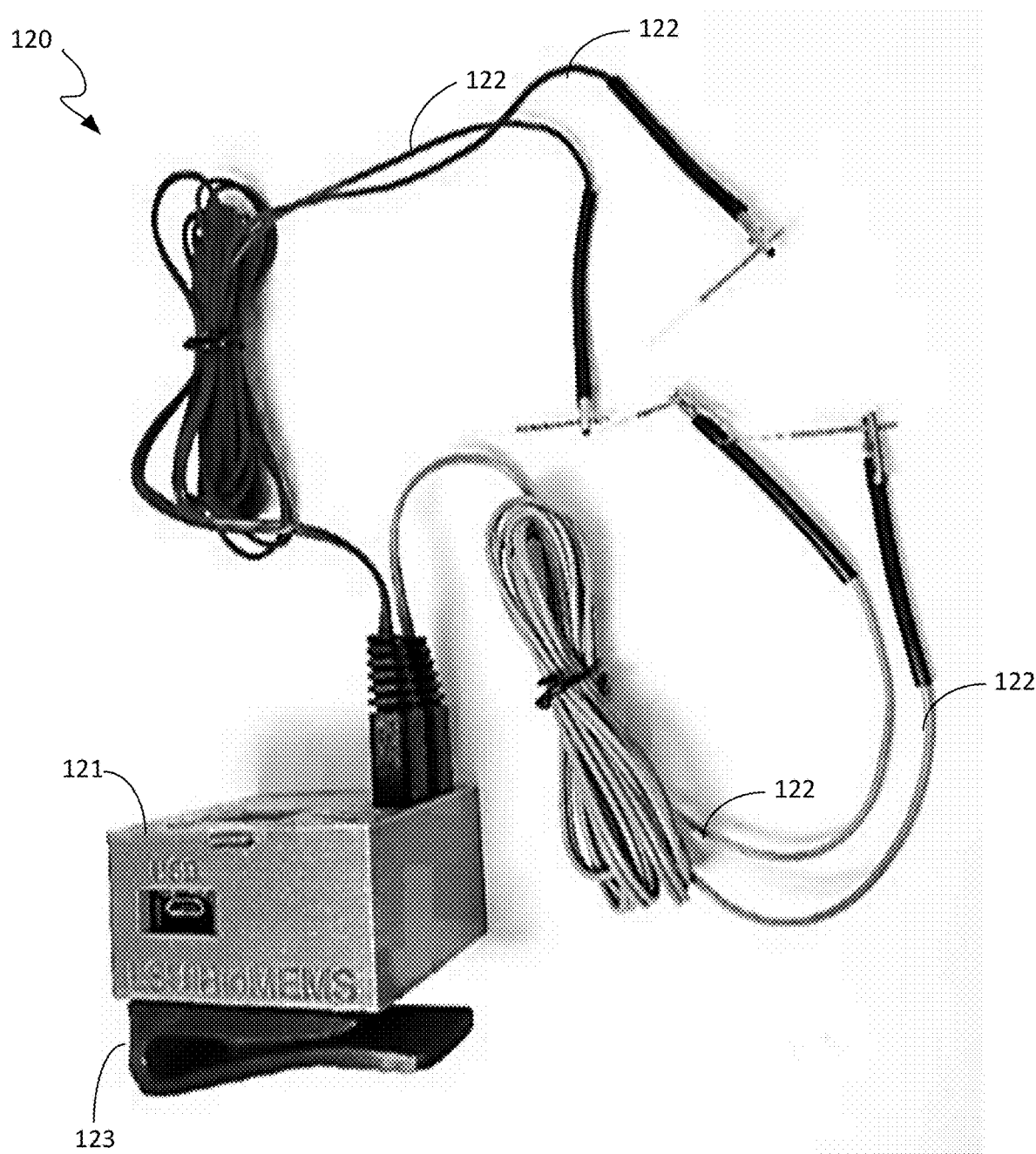
FIG. 10 is a photograph of a two-channel wearable neurostimulator device prototype that incorporates the EA circuit shown in FIG. 9 in accordance with a representative embodiment.

FIG. 10 is a photograph of a two-channel wearable neurostimulator device prototype 120 that incorporates the EA circuit 120 shown in FIG. 9 in accordance with a representative embodiment. The case 121 for this device was 55 mm×48 mm×30 mm. Testing was performed using a 2000 mAh 3.7 V lithium polymer battery. The case 121, leads 122, and attachment device 123 (e.g., a collar clip) are shown in FIG. 10. The case 121 has a shape, size and weight selected to allow the wearable neurostimulator device 121 to be easily and comfortably worn on the patient's body. For example, the case 121 may be attached by the attachment device 123 or by any suitable attachment device to the patient's belt in the case where the patient is a human being, or to a collar in the case where the patient is an animal.

Two-Channel Operation Verification

The wearable neurostimulator device prototype 120 was tested to operate in single-channel, and simultaneous two-channel mode with independent voltage and frequency control. Output with either Channel 1, Channel 2, or simultaneous output is shown in FIGS. 4.12(a). The calculated output of the oscilloscope probes that represents the system channel 1 and channel 2 is shown in FIG. 12(b). Channel 1 was set to 4V output amplitude and 100 Hz frequency, and channel 2 was set to 2.5 V output with 50 Hz frequency. The independent stimulation duration timer was also tested and found to be working properly. However, an issue with the previously used 500 mAh 3.7V battery and power supply was found. A drop in maximum amplitude voltage was seen when both channels were set to output simultaneously. This is because the battery supplies power simultaneously to both circuits. A 30 uF capacitor bank was used as a decoupling capacitor, but this issue was still present. Using the 2000 mAh battery showed no problem. Further revision to the power supply, such as a larger decoupling capacitor or bigger battery, would allow for this issue to be resolved.

Figure 11:
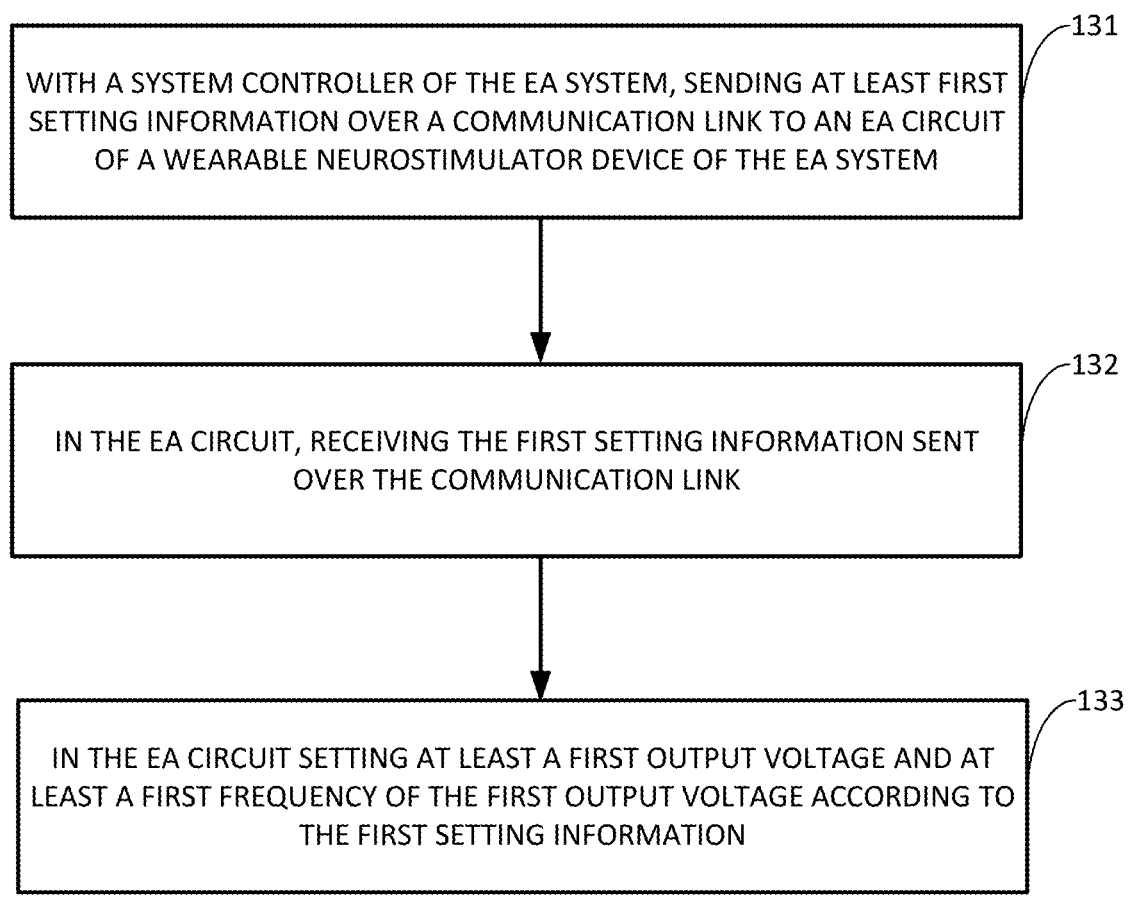
FIG. 11 is a flow diagram depicting the EA method in accordance with a representative embodiment.

FIG. 11 is a flow diagram depicting the EA method in accordance with a representative embodiment. With a system controller of the EA system, at least first setting information is sent over a communication link, as indicated by block 131. In an EA circuit of a wearable neurostimulator device of the EA system worn by a patient, the first setting information sent over the communication link by the system controller is received in the EA circuit, as indicated by block 132. In the EA circuit of the wearable neurostimulator device, at least a first output voltage of the EA circuit and a first frequency of the first output voltage are set according to the received first setting information, as indicated by block 133. At least a first pair of electrically-conductive acupuncture needles is electrically coupled to a first pair of output terminals of the EA circuit such that the first output voltage is output to the first pair of electrically-conductive acupuncture needles.

CONCLUSIONS

The field of EA treatment and research has been slowed down due to a lack of modern treatment devices that allow for precise controllability and reproducibility. Stimulation machines are large and cumbersome which in turn leads to difficult clinical conditions and research problems. For clinicians this means that treatment protocols are hard to reproduce within the same patient, and animals have to be restrained or sedated in the case of veterinary patients. Stress that arises from restraining has an impact on the outcome of EA treatment. These problems can be tackled by designing EA stimulation machines with the clinician and patient in mind.

An electro-acupuncture stimulator was designed in order to address these problems. The system is shown to operate via Bluetooth connection with a smartphone, and its output voltage control, stimulation frequency control, and battery life are characterized. The output of the device was measured in PBS solution using acupuncture needles as electrodes. The device is used in an EA animal study to verify its capability for EA stimulation, and it is shown to have less user error than dry needle acupuncture. A significant advantage of this stimulator lies in its connectivity to a smartphone. The smartphone is used to monitor device status and output settings. This feature allows for treatment protocols to be easily reproduced by other scientists and clinicians. A 2-channel implementation of the device was shown and the 2-channel operation was demonstrated. The requirements per channel are also outlined for further implementations with more channels. This approach could also benefit from dedicated PWM drivers such that each driver can allow for more output channels.

The smartphone can also be used to implement secure access for doctors, and allow them to store their patient data and treatment data in the device. Novel applications include programming of the system for at-home EA treatment. Further work involves implementing the advanced smartphone features for the device, and investigating possibilities for the device to be used in further EA research and clinical treatment.

The methods described above that are performed by the smartphone 4 and by the EA circuit 10 are typically performed in software or firmware, or a combination thereof, executed by one or more processors (not shown) of the smartphone 4 or by the processor 15 of the EA circuit 10. It should be noted, however, that some or all portions of these method may be performed solely in hardware or in a combination of hardware, software and/or firmware. Any software and/or firmware that is used for these purposes is stored in a suitable non-transitory memory device, such as a random access memory (RAM) device, a read only memory (ROM) device, various forms of RAM and ROM, a flash memory device, an optical storage medium, a magnetic storage medium, etc.

It should be noted that many variations may be made to the EA system 1 within the scope of the inventive principles and concepts. For example, although the wearable neurostimulator device 2 has been described as having the circuits 10 and 100 shown in FIGS. 2 and 9, respectively, other circuits may be used for this purpose. Thus, the inventive principles and concepts are not limited to the representative embodiments described herein. Although the inventive principles and concepts have been illustrated and described in detail in the drawings and in the foregoing description, such illustration and description are to be considered illustrative or exemplary and not restrictive; the invention is not limited to the disclosed embodiments. Other variations to the disclosed embodiments can be understood and effected by those skilled in the art, from a study of the drawings, the disclosure, and the appended claims.

What is claimed is:

1. An electro-acupuncture (EA) system for performing EA on a patient via acupuncture needles, the EA system comprising:
   a wearable neurostimulator device comprising:
      a casing,
      an EA circuit mechanically coupled to the casing, the EA circuit comprising a stimulator circuit configured to generate an output pulse waveform having a first output voltage via a first pair of output terminals, a boost converter circuit configured to control output level via pulse-width modulation (PWM), and a high-voltage (HV) switch circuit electrically coupled between the boost converter circuit and the stimulator circuit, and
      an attachment device mechanically coupled to the casing and adapted to removably secure the wearable neurostimulator device to the patient;
   at least a first pair of electrically-conductive acupuncture needles directly electrically coupled to the first pair of output terminals of the EA circuit; and
   a system controller in communication with the EA circuit of the wearable neurostimulator device via a communication link, the system controller controlling the EA circuit by sending at least a first set of setting information to the EA circuit over the communication link to cause the EA circuit to output the first output voltage at a first frequency from the first pair of output terminals in accordance with the first set of setting information selected by the system controller.

2. The EA system of claim 1, wherein the system controller comprises a smartphone and wherein the communication link is a wireless communication link.

3. The EA system of claim 2, wherein the communication link is a Bluetooth communication link.

4. The EA system of claim 3, wherein the Bluetooth communication link is a Bluetooth Low Energy (BLE) communication link.

5. The EA system of claim 2, wherein the smartphone comprises at least a first processor configured to perform an EA application program that processes information input to the smartphone by a user and sends said at least a first set of setting information to the EA circuit via the wireless communication link to control the EA circuit in accordance with the information input to the smartphone by the user.

6. The EA system of claim 5, wherein the EA circuit comprises:
   at least a second processor configured to control operations of the EA circuit based on said at least a first set of setting information received by the EA circuit from the smartphone.

7. The EA system of claim 6, wherein the EA circuit further comprises:
   a Bluetooth module electrically coupled with the second processor, the Bluetooth module performing a Bluetooth protocol that processes communications sent by the smartphone to the EA circuit and outputs said at least a first set of setting information to the second processor, and wherein the second processor is configured to execute a settings algorithm that sets the first output voltage and the first frequency of the EA circuit according to said at least a first set of setting information output by the Bluetooth module to the second processor.

8. The EA system of claim 7, wherein:
   the boost converter circuit is electrically coupled with at least the second processor; and
   the HV switch circuit is electrically coupled with the second processor.

9. The EA system of claim 2, wherein the EA circuit is an N-channel configuration, where N is a positive integer that is greater than one, the EA circuit further comprising a second stimulator circuit configured to provide a second output voltage via a second pair of output terminals, a second boost converter circuit configured to control output level via pulse-width modulation (PWM), and a second HV switch circuit electrically coupled between the second boost converter circuit and the second stimulator circuit, the EA system further comprising:
   at least a second pair of electrically-conductive acupuncture needles electrically coupled to the second pair of output terminals of the EA circuit, and wherein the system controller controls the EA circuit to cause the EA circuit to output at least the second output voltage selected by the system controller at a second frequency selected by the system controller from the second pair of output terminals, the second output voltage and the second frequency being set by the EA circuit in accordance with a second set of setting information sent by the system controller and received by the EA circuit.

10. The EA system of claim 9, wherein the first and second output voltages are equal to or unequal to one another and the first and second frequencies are equal to or unequal to one another.

11. The EA system of claim 9, wherein the smartphone comprises at least a first processor configured to perform an EA application program that processes information input to the smartphone by a user and sends at least the first and second sets of setting information to the EA circuit via the wireless communication link to control the EA circuit in accordance with the information input to the smartphone by the user.

12. The EA system of claim 11, wherein the smartphone further comprises:
   a memory device in communication with the first processor, the memory device storing location specific setting information input to the smartphone by the user, the location specific setting information being associated with use of the EA system at a defined location, and wherein when the smartphone is powered on at the defined location, the location specific setting information is retrieved from the memory device and sent by the smartphone to the wearable neurostimulator device to cause the first output voltage and the first frequency to be set according to the location specific setting information.

13. A method for performing electro-acupuncture (EA) on a patient with an EA system comprising a system controller and a wearable neurostimulator device, the method comprising:
   sending, with the system controller of the EA system, at least a first set of setting information to the wearable neurostimulator device over a communication link;
   receiving, by an EA circuit of the wearable neurostimulator device, the first set of setting information sent over the communication link by the system controller, the EA circuit comprising a stimulator circuit configured to generate an output pulse waveform having a first output voltage via a first pair of output terminals, a boost converter circuit configured to control output level via pulse-width modulation (PWM), and a high-voltage (HV) switch circuit electrically coupled between the boost converter circuit and the stimulator circuit; and setting, in the EA circuit of the wearable neurostimulator device, at least the first output voltage of the EA circuit and a first frequency of the first output voltage according to the received first set of setting information; and output, by the EA circuit, the first output voltage at the first frequency via at least a first pair of electrically-conductive acupuncture needles directly electrically coupled to the first pair of output terminals.

14. The method of claim 13, wherein the system controller comprises a smartphone and wherein the communication link is a wireless communication link.

15. The method of claim 14, wherein the communication link is a Bluetooth communication link.

16. The method of claim 15, wherein the Bluetooth communication link is a Bluetooth Low Energy (BLE) communication link.

17. The method of claim 14, wherein the smartphone comprises at least a first processor configured to perform an EA application program that processes information input to the smartphone by a user and sends said at least a first set of setting information to the EA circuit via the wireless communication link to control the EA circuit in accordance with the information input to the smartphone by the user.

18. The method of claim 13, wherein the EA circuit has N channels for supplying N output voltages to N pairs of electrically-conductive acupuncture needles, where N is a positive integer that is greater than one, the method further comprising:

sending, with the system controller of the EA system, N-1 additional sets of setting information over the communication link;

receiving, by the EA circuit of the wearable neurostimulator device, the N-1 additional sets of setting information sent over the communication link by the system controller, the EA circuit further comprises N-1 additional channels each comprising a corresponding stimulator circuit configured to provide a corresponding output voltage via a corresponding pair of output terminals, a corresponding boost converter circuit configured to control output level via pulse-width modulation (PWM), and a corresponding HV switch circuit electrically coupled between the corresponding boost converter circuit and the corresponding stimulator circuit; and setting, in the EA circuit of the wearable neurostimulator device, N-1 corresponding output voltages for the N-1 additional channels of the EA circuit and N-1 frequencies of the N-1 corresponding output voltage according to the received N-1 sets of setting information, respectively, and wherein N-1 pairs of electrically-conductive acupuncture needles are electrically coupled to N-1 corresponding pairs of output terminals, respectively, of the EA circuit such that the N-1 corresponding output voltages are output to the N-1 pairs of electrically-conductive acupuncture needles.

19. The method of claim 18, wherein N is greater than two.

20. The method of claim 18, wherein the first output voltage is equal to a first of the N-1 corresponding output voltages and unequal to a second of the N-1 corresponding output voltages and the first frequency is equal to the frequency of the first of the N-1 corresponding output voltages and unequal to the frequency of the second of the N-1 corresponding output voltages.

* * * * *